United States Patent [19]

Hellberg

[11] 4,222,123

[45] Sep. 16, 1980

[54] MOUNTING A FACE SHIELD AT A PROTECTIVE HELMET

[75] Inventor: Arne Hellberg, Gråbo, Sweden

[73] Assignee: Hellberg Protection AB, Sweden

[21] Appl. No.: 16,177

[22] Filed: Feb. 28, 1979

[30] Foreign Application Priority Data

Mar. 7, 1978 [SE] Sweden .............................. 7802554

[51] Int. Cl.² .......................... A42B 1/06; A42B 3/00
[52] U.S. Cl. ...................................................... 2/10
[58] Field of Search ................... 2/424, 423, 422, 10, 2/9, 8, 453

[56] References Cited

U.S. PATENT DOCUMENTS

| | | | |
|---|---|---|---|
| 2,588,553 | 3/1952 | McWethy | 2/453 X |
| 2,801,420 | 8/1957 | Malcom, Jr. | 2/10 X |
| 3,067,426 | 12/1962 | Tompkins | 2/9 X |
| 3,147,487 | 9/1964 | Hoeftman | 2/8 |
| 3,332,086 | 7/1967 | Simpson et al. | 2/10 X |
| 4,022,466 | 5/1977 | Kaiser | 2/9 X |
| 4,117,553 | 10/1978 | Bay | 2/10 |

FOREIGN PATENT DOCUMENTS 1174669 11/1958 France .......................................... 2/10

*Primary Examiner*—Peter P. Nerbun
*Attorney, Agent, or Firm*—Holman & Stern

[57] ABSTRACT

A protective helmet is provided with two externally located pockets for receiving fittings adapted to carry accessories. An elongate, resilient arm at each fitting extends towards the front of the helmet, and forms one component in a pivot joint. The face shield is provided with two mounting tabs, to be attached to the elongate arms.

Each pivot joint comprises a stud insertable in a bore, the mounting being facilitated by flexing the resilient arms outwards, and the tab is retained into engagement with the associated arm by a wart at the tab abutting against the shell of the helmet.

At least one of the tabs is provided with a transversely running ledge, and the end of the arm is defined by two side edges arranged at right angles to each other. In an inactive position the ledge rests against one of said edges, which in mounted position runs substantially horizontally. When the shield is swung to active position the ledge abuts against the other edge, the relative positions being selected so the ledge tardily passes the corner between the side edges, when the shield is swung from one position to the other.

5 Claims, 6 Drawing Figures

MOUNTING A FACE SHIELD AT A PROTECTIVE HELMET

BACKGROUND OF THE INVENTION

Protective helmets may be classified differently depending upon the requirements imposed upon the helmet. In order that a helmet be referred to the highest class, certain countries stipulate that there must be no bolts or holes piercing the shell of the helmet. Through-bolts are considered as a safety risk, as they can conduct electric current from the outside of the shell to its inside. The need to dispense with the use of such bolts brings about certain difficulties with respect to the attachment of various accessories to the helmet. This applies for instance to the mounting of a face shield, which must be pivotable between two positions, one active position in front of the face, and one retracted, rest position. It is furthermore important that the face shield is designed so as to permit an easy mounting and dismounting, as it is desirable to remove the shield when it is not required for the work at hand, and it furthermore is advantageous to be able to substitute one shield for an other, as called for by the work to be performed.

SUMMARY OF THE INVENTION

The aim of the present invention is to solve the problem above indicated. A mounting means according to the invention is characterized that the helmet, at two juxtaposed portions of its circumference, is provided with two external, upwardly open pockets, and that fittings for the face shield are each provided with a first arm adapted to be inserted in one of said pockets, and a second, elongate and resilient arm, adapted, in mounted position, to be directed towards the front of the helmet. The mounting tabs at the face shield are formed to be pivotably connected to said second arms, and each mounting tab is retained into engagement with the associated second arm by a distance member provided between the tab and the shell of the helmet. The pivot preferably comprises a stud at one of the cooperating joint components, which freely extends into a mating bore in the other component, the distance member being formed as a wart at the face of the tab turned towards the helmet. The second arm of the pivot is preferably, outside of the pivot defined by two side edges abutting about at right angles to each other, and at least one of the mounting tabs of the face shield is provided with an outwardly directed projection adapted to cooperate with either of said side edges, depending upon the occasional position of the face shield. The projection is advantageously designed as a ledge running transversely across the mounting tab.

DESCRIPTION OF A PREFERRED EMBODIMENT

Figure 1:
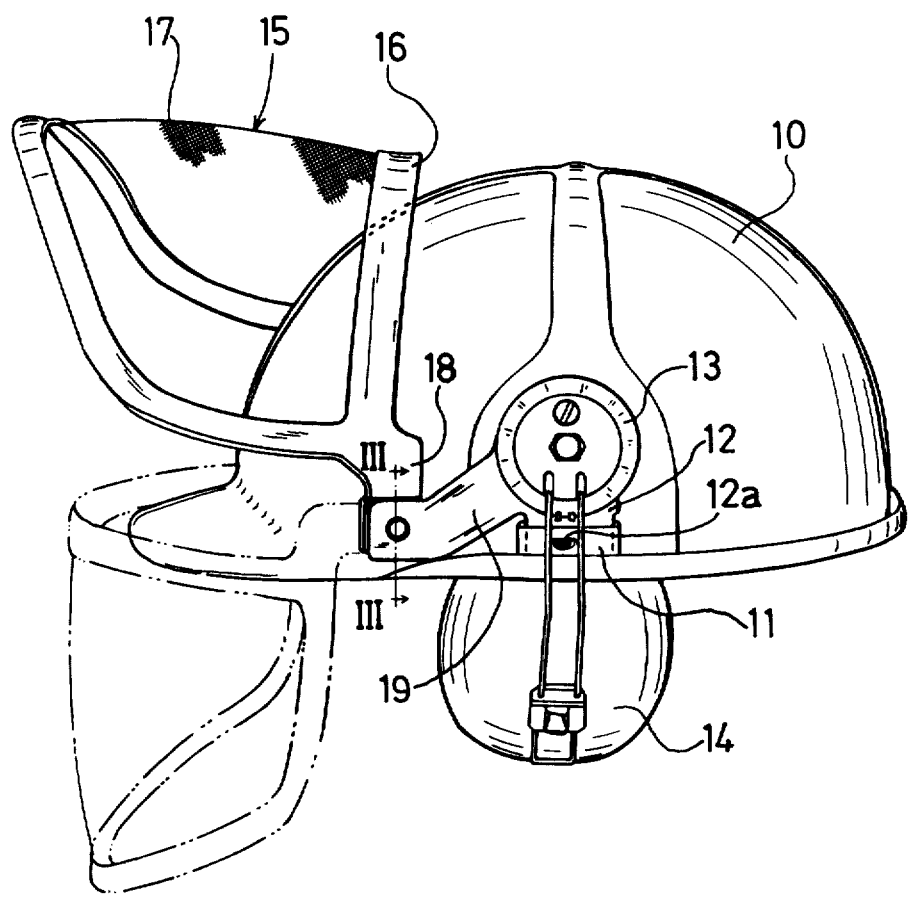
FIG. 1 shows an elevation of a protective helmet having a face shield mounted according to the invention.

The protective helmet shown in FIG. 1 is generally denoted by 10. It is manufactured of plastics and is, to each side provided with an external pocket 11 located about above the ears of the wearer. In each of those pockets a first arm 12 of a fitting 13 is insertable, said fitting being adapted to carry accessories to be mounted at the helmet. FIG. 1 shows earmuffs 14, and a face shield 15 attached to the helmet by means of the fittings 13. The first arms 12 are provided with resilient tongues 12a engaging into openings in the outward wall of pocket 11 to securely retain fittings 13 at the helmet.

A face shield 15 may, depending upon the work to be performed, be formed as, or include a transparent sheet, or may be formed largely from wire mesh.

The one shown in FIG. 1 comprises a frame 16 supporting a piece of wire mesh 17, and two mounting tabs 18, which will be described more in detail herebelow. FIG. 1 shows in full lines the shield raised to a rest position, on top of the helmet, and in broken lines the shield swung down to an active position in front of the wearer's face.

Each fitting 13 is provided with a second, elongate arm 19, which in mounted position of the fitting extends towards the front of the helmet. Due to the basically oval shape of the lower rim of the helmet, the distal ends of an arm 19 will be located further away from the shell of the helmet than the main body of the fitting, which facilitates the mounting of the face shield.

The face shield 15 is attached to the fittings by means of an open stud-in-bore joint in a manner to be described below.

Figure 2:
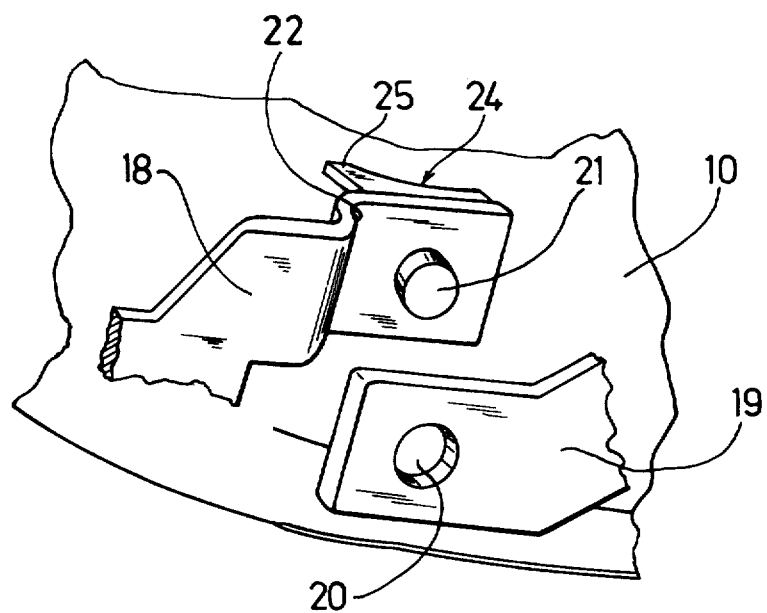
FIG. 2 shows, on a larger scale, parts of the joint between a mounting tab at the shield and a fitting at the helmet.

FIG. 2, on a larger scale, shows a resilient arm 19 of a fitting 13, a mounting tab 18 of the face shield and a portion of helmet 10. When mounting the face shield 15, the resilient arms 19 are flexed outwardly, and the mounting tabs 18 are introduced between the helmet 10 and arms 19. The latter are each provided with a through-bore 20 for a stud 21 at the associated mounting tab 18. The latter is furthermore provided with a projection 22, the function of which will be described below.

Figure 3:
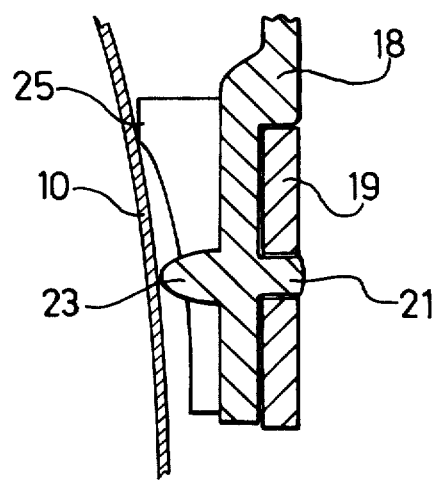
FIG. 3 shows a section along line III—III in FIG. 1 illustrating the joint between the mounting tab and the fitting.

FIG. 3 shows a section through the joint and illustrates how the mounting tab 18 is retained between the helmet 10 and the resilient arm 19 of the fitting 13. The mounting tab 18 is provided with a projecting wart 23, which is aligned with stud 21 and is resiliently forced against the shell of the helmet by arm 19 of fitting 13. The wart 23 serves as a main distance member between the helmet and the tab, and is formed with a domed top to reduce the friction between the tab and the shell when swinging the face shield.

There is also an auxiliary distance member 24 at the inward face of the tab 18, which will engage the shell of the helmet when the face shield is brought to its rest position. This distance member is formed as a shelf along the edge of the tab, which faces upwards, when the shield is in active position. The ledge 24 is at its end remote from fitting 13 provided with a projecting ear 25.

The shell of the helmet is inclined inwardly in the direction towards the crown of the helmet, and as will be explained below the ear 25 will apply an extra pressure upon the tab, when the shield is swung to its rest position.

It is of course important that the face shield does not inadvertedly swing down to its active position due to its own weight.

Projection 22 is formed as a ledge running transversely across the mounting tab, and is obtained by off-setting part of the latter from the shield frame 16. The distal end of arm 19 is defined by an upwardly facing side edge 26 and a forwardly facing side edge 27, which abut against each other about at right angles at a corner 28.

The bore 20 is located so ledge 22 tardily will pass corner 28 when the shield is swung from its rest to its active position, or vice versa.

Figure 4:
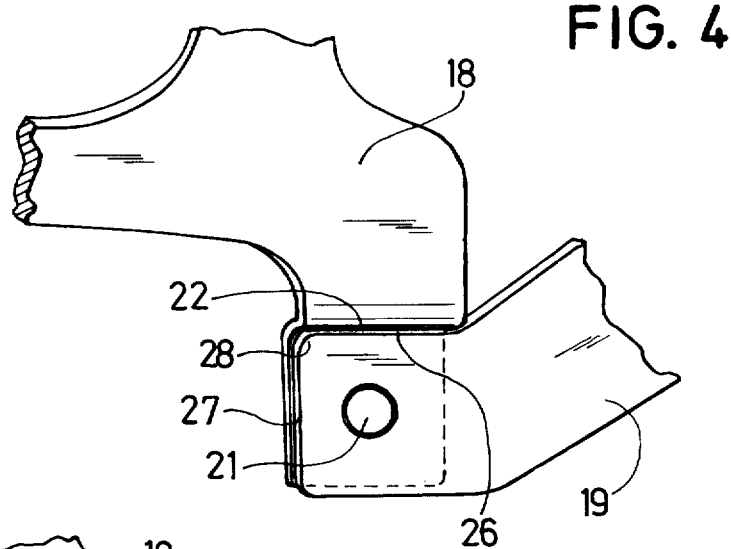
FIGS. 4-6 show positions of the tab and the fitting during various swinging positions.

In the inactive position ledge 22 at the mounting tab 18 will, as is shown in FIG. 4, rest upon the upwardly facing side edge 26 at resilient arm 19. In this position wart 23 and ear 25 abut against the shell of the helmet and exert a pressure to retain the shield in raised position.

Occasionally it may be desirable to make ear 25 so long that it flexes arm 19 sufficient outwardly to lift wart 23 away from the shell of the helmet.

Figure 5:
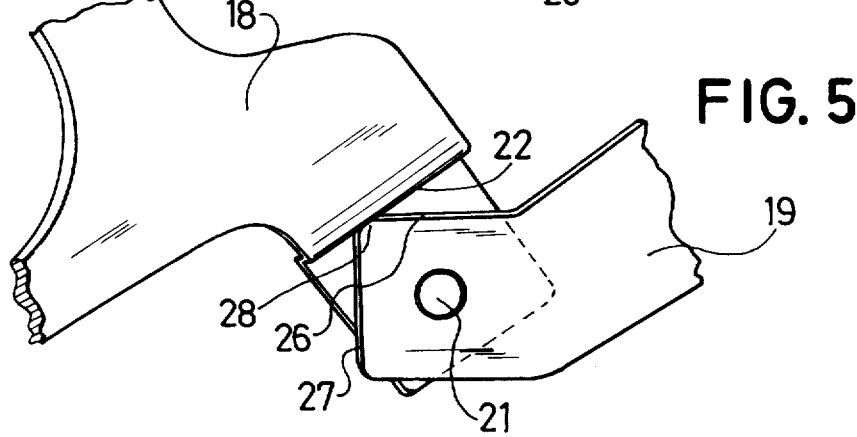

When the face shield is to be lowered, it is pulled down by hand, whereby ledge 22 is forced past corner 28 at arm 19, as is shown in FIG. 5.

Figure 6:
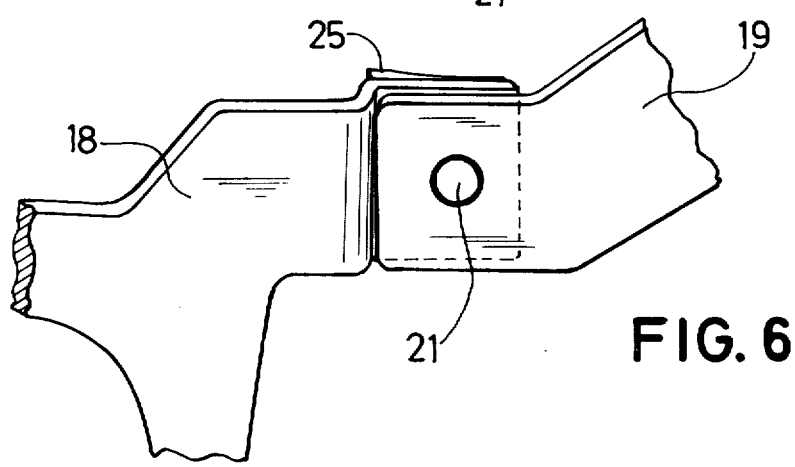

FIG. 6 shows the face shield in active position, in which projection 22 abuts against the vertical side edge 27 of arm 19.

FIG. 6 shows the components with the face shield in fully lowered position.

Due to the cooperation between ledge 22 and the side faces 26 and 27 of arm 19, the face shield is retained in its raised, as well as in its lowered position.

A joint according to the invention permits a simple way of attaching the face shield 15 to the fittings 13, and also to dismount the shield and to substitute the same for an other one.

As is mentioned above the distal ends of arms 19 will be located somewhat outside the juxtaposed portions of the shell. The face shield generally has some degree of resiliency and is bent into a shape suited for fitting to the arms 19. These are flexed slightly outwards, the mounting tabs are introduced into the spaces between the arms and the shell, and the studs 21 are snapped into bores 20. The tabs will then, as described above, be retained, due to the inward pressure of arms 19 and the engagement of wart 23 and ear 25 against the shell.

Dismounting of the shield is easily obtained by flexing arm 19 outwards and withdrawing the studs 21 from bores 20.

The invention is not limited to the embodiment described above, and a number of modifications may be performed within the scope of the appended claims.

The stud 21 and the wart 23 must not necessarily be formed integrally with the mounting tab 18, but may be substituted by a bolt, the head of which, in mounted position, abuts against the shell of the helmet 10, while its shank passes through bores in mounting tab 18, as well as in arm 19 of the fitting.

The joint between the fitting and the mounting tab may also be formed so the stud is formed integrally with resilient arm 19, while the mounting tab 18 is provided with a blind bore.

What I claim is:

1. Means for releasably mounting a swingable face shield on a protective helmet having a hard shell being defined by a lower rim including a front portion, comprising two external, upwardly open pockets at juxtaposed portions of the lower rim of the helmet,
   two fittings, each having a first arm adapted to be inserted in one of said pockets, as well as a second, elongate and resilient arm adapted, in mounted position, to extend towards the front of said rim,
   a face shield having two mounting tabs,
   a stud-in-bore joint to releasably mount each of said mounting tabs inside of an associated second arm, and
   a distance member acting between the inward face of each mounting tab and a juxtaposed portion of the helmet shell to force each mounting tab against its associated resilient second arm.

2. The means according to claim 1, in which said joint comprises a stud on said mounting tab and a mating bore in said second arm, and the distance member is formed as a wart on the inward face of the tab towards the front portion of said helmet.

3. The means according to claim 1, in which said second arm of the fitting, outside of the joint, is defined by two side edges abutting about at right angles to each other, and in that at least one of said mounting tabs of the face shield is provided with an outwardly directed projection adapted to cooperate with either of said side edges, depending upon the occasional position of the face shield.

4. The means according to claim 3, in which one of said side edges, in mounted position, runs substantially horizontally, and that the projection at the tab is formed as a transverse, substantially straight ledge, located so it, during a swinging movement of the shield from one position to an other, tardily passes the corner between the two side edges.

5. The means according to claim 1, further including an auxiliary distance member on the inward face of at least one of said mounting tabs formed as a ledge along the edge of the tab which is substantially horizontal when said shield is brought to active position, said ledge having a projecting ear at its inner end to engage said helmet when in the raised position.

* * * * *